United States Patent [19]
Herbert

[11] Patent Number: 5,779,649
[45] Date of Patent: Jul. 14, 1998

[54] SURGICAL SUCTION WAND WITH FILTER

[75] Inventor: H. Nicholas Herbert, San Juan Capistrano, Calif.

[73] Assignee: Pabban Development, Inc., Irvine, Calif.

[21] Appl. No.: 768,751

[22] Filed: Dec. 17, 1996

[51] Int. Cl.$^6$ .................................................. A61B 5/00
[52] U.S. Cl. ........................... 600/571; 604/49; 604/319
[58] Field of Search ............................. 600/562, 565.5, 600/571, 573, 580; 604/317–321

[56] References Cited

U.S. PATENT DOCUMENTS

| | | |
|---|---|---|
| 3,889,657 | 6/1975 | Baumgarten. |
| 4,393,879 | 7/1983 | Milgrom .................................. 128/758 |
| 4,468,217 | 8/1984 | Kuzmick et al. ........................ 604/48 |
| 4,801,292 | 1/1989 | Watson .................................... 604/36 |
| 4,813,931 | 3/1989 | Hauze ..................................... 604/54 |
| 4,870,975 | 10/1989 | Cronk et al. ........................... 128/749 |
| 4,886,492 | 12/1989 | Brooke .................................... 604/49 |
| 4,957,492 | 9/1990 | McVay .................................... 604/319 |

*Primary Examiner*—Max Hindenburg
*Attorney, Agent, or Firm*—G. Donald Weber, Jr.

[57] ABSTRACT

A surgical suction wand comprising a generally tubular body with a hollow tip at one end thereof, a cap releasably closing the other end of the tubular body, and a filter member within the body and joinable to the under surface of the cap. The hollow tip communicates with the interior of the body. A tubular connector is mounted externally on the cap and communicates with the interior of the cap and the body. The filter member within the body defines a first chamber between the filter member and the body and a second chamber within the filter member which communicates with the tubular connector through the cap. One or more apertures through the filter member permit limited communication between the first and second chambers. The cap has positioning means therein for locating and securing one end of the filter member within the cap and body. The other end of the filter member is closed and disposed in the body adjacent to the hollow tip. In operation, waste material flows through the tip into the hollow interior of the body wherein particulate waste is trapped in the first chamber by the filter member while fluids pass through the apertures in the filter member and out of the suction wand via the tubular connector at the cap. The filter member is easily removed (along with the cap), cleaned and returned to the interior of the tubular body as required.

20 Claims, 1 Drawing Sheet

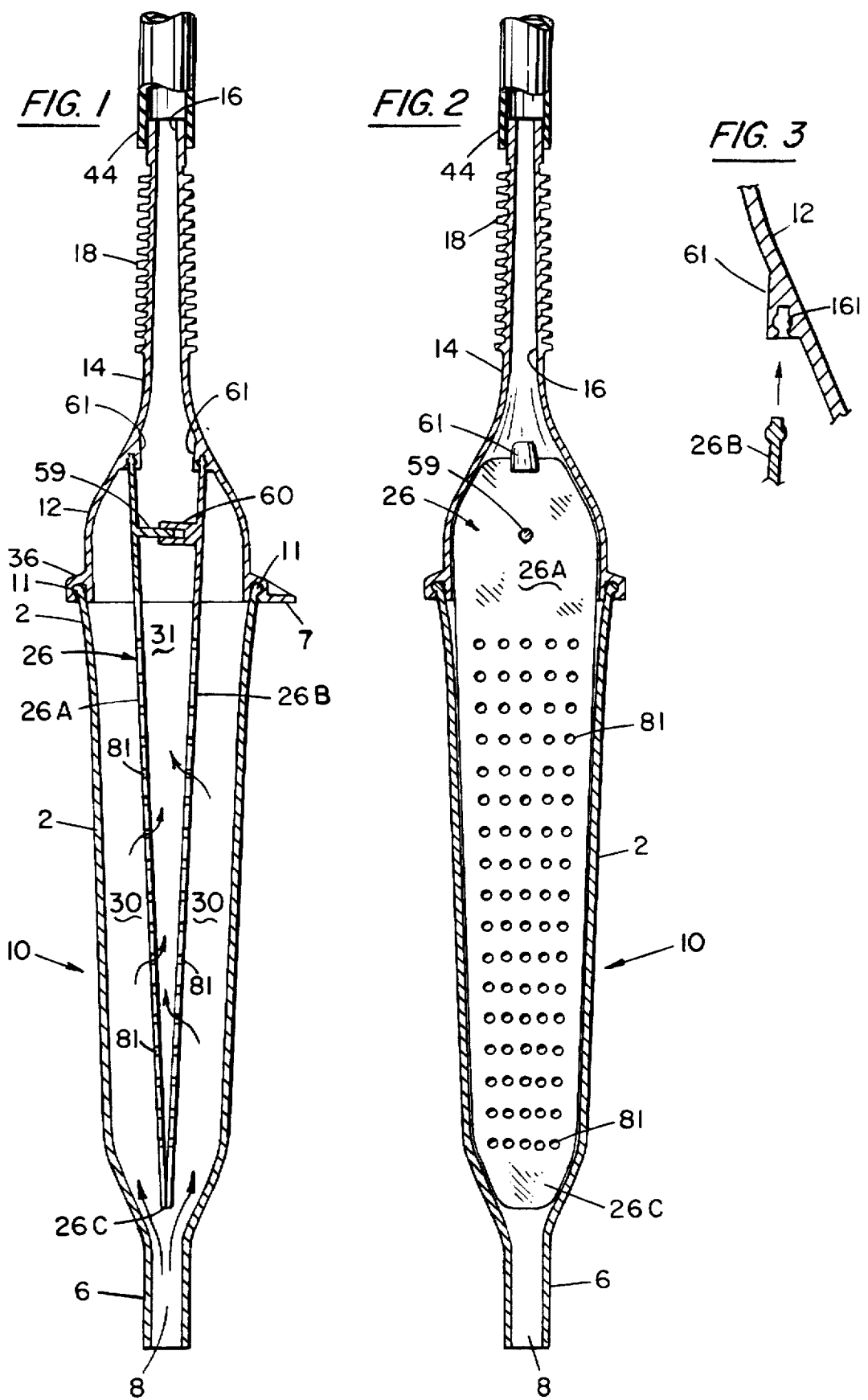

SURGICAL SUCTION WAND WITH FILTER

BACKGROUND

1. Field of the Invention

The present invention relates to surgical suction wands such as are used to remove waste matter from the body during surgery, in general, and to a surgical suction wand having a filter which is easily removed, cleaned and replaced in the body, in particular.

2. Prior Art

In many surgical procedures, it is necessary to remove effluvia and detritus from a surgical site in the body. In orthopedic surgery, for example when replacing a hip or knee joint, it is often necessary to clean out the center of a bone prior to fitting the prosthesis. As in most surgeries, it is common practice to utilize a suction wand and associated suction source to remove unwanted gelatinous blood, bone splinters, tissue and the like.

The systems to effect this practice commonly comprise a suction source acting through a container and a length of tubing to the hand-held suction tip itself whereby solid and liquid waste are drawn through the suction tip, along the tubing and into the container.

However, the nature of the waste material so removed from a patient is such that the suction tip, as well as the tubing therefrom, may become clogged by bits of tissue and other matter. It is then necessary to clean out the suction line or the suction tip (or wand) in order to continue the surgical procedure. This is clearly a time-consuming process in a time-sensitive activity. In addition, sterility at the wound site could be compromised.

In the past, it has been proposed to provide a surgical suction tip or wand incorporating a removable filter element such as disclosed in the U.S. Patents set forth in the Prior Art Statement. However, these filter elements and the suction wands are often relatively complex in construction and expensive.

PRIOR ART STATEMENT

U.S. Pat. No. 2,822,808; DISPOSAL SPECIMEN COLLECTOR; G. D. Boone. This patent is directed to a device having two co-axial components with O-rings therebetween to establish an airtight engagement thereof.

U.S. Pat. No. 4,468,217; SURGICAL SUCTION TIP WITH FILTER; K. M. Kuzmick et al. This patent is directed to a surgical suction tip with a tapered housing and removable filter device therein.

U.S. Pat. No. 4,813,931; PEDIATRIC SUCTION SYSTEM AND METHOD WITH FILTER; D. R. Hauze. This patent is directed to a pediatric suction system with a filter which prevents reverse travel of contaminants from the vacuum tube to a suction tube.

U.S. Pat. No. 4,083,706; STERILE TRAP ACCESSORY FOR USE WITH SURGICAL ASPIRATOR; C. W. Wiley. This patent is directed to a trap accessory which is coupled between a suction conduit and an aspirator.

U.S. Pat. No. 4,767,404; SURGICAL SUCTION DEVICE HAVING A PERFORATED SLEEVE; D. Renton. This patent is directed to a suction device with a perforated suction tip for removal of surgical debris with reduced clogging.

U.S. Pat. No. 4,886,492; SURGICAL SUCTION TIP WITH FILTER; G. M. Brooke et al. This patent is directed to a surgical tip which includes a tubular body and a hollow tip along with a cap releasably closing the other end of the body.

U.S. Pat. No. 5,409,013; TISSUE REMOVAL ASSEMBLY; T. P. Clement. This patent is directed to a suction and irrigation lavage with a cannula having a distal end insertable into a patient's body and includes a cutting edge.

U.S. Pat. No. 4,966,584; SUCTION ASPIRATOR WITH NOISE-CONTROL VALVE; L. P. Nguyen. This patent is directed to a suction aspirator with a built-in interrupting valve to control the vacuum suction flow and the noise thereof.

U.S. Pat. No. 5,141,504; FLUID RECOVERY SYSTEM WITH STOPCOCK SUCTION CONTROL; S. A. Herweck et al. This patent is directed to a drainage device which includes a vessel having a plurality of sub-chambers which are directed to the regulation of drainage and drainage flow.

U.S. Pat. No. 5,248,297; SUCTION TUBE FOR USE OF SURGICAL OPERATION; H. Takasee. This patent is directed to a surgical suction tube which has a relief path formed between the suction tube body and a fluid supply tube.

U.S. Pat. No. 5,437,651; MEDICAL SUCTION APPARATUS; R. J. Todd et al. This patent is directed to an apparatus and method having an absorbent connected to a suction source for absorbing and collecting blood and other fluids.

U.S. Pat. No. 4,060,107; METHOD AND APPARATUS FOR COLLECTING FLUIDS; H. Naftulin. This patent is directed to an apparatus which includes an outer vaccum chamber and a flexible container disposed therein for collecting fluids in the flexible chamber.

U.S. Pat. No. 4,957,492; APPARATUS FOR COLLECTING AND HANDLING TISSUE DURING UTERINE EVACUATION PROCEDURE; W. P. McVay. This patent is directed to an apparatus including a tissue trap placed in advance of the collection bottle for filtering out and collecting pathological tissue specimens.

U.S. Pat. No. 5,244,458; COLLAGEN GATHERING APPARATUS; K. Takasu. This patent is directed to an apparatus for collecting collagen including a tissue crusher having a suction pipe and a vacuum pump.

U.S. Pat. No. 5,098,418; ASPIRATOR DEVICE FOR BODY FLUIDS; C. A. Maitz et al. This patent is directed to an aspirator suction device for removing body fluids and includes two elongated tubes, one having a tapered end for insertion into body cavities, the other having a mouthpiece for mouth actuation.

U.S. Pat. No. 4,795,448; SUCTION COLLECTION SYSTEM; G. R. Stacey, et al. This patent is directed to a suction collection system which includes a cylindrical evacuating chamber with a top sealing cap and suction port therein.

U.S. Pat. No. 5,035,688; POLYP OR CELL BLOCK COLLECTION INSTRUMENT; M. Inui. This patent is directed to a polyp or cell collecting instrument adapted for use with an endoscope and having a suction passage.

U.S. Pat. No. 4,487,600; ADJUSTABLE SUCTION DEVICE FOR MEDICAL USE; A. W. Brownlie et al. This patent is directed to an adjustable disposable device which includes a handle, a rigid outer tube with an oblique bend and a co-acting flexible innertube.

U.S. Pat. No. 4,753,634; FAT COLLECTION SYRINGE; G. W. Johnson. This patent is directed to a syringe which has a barrel with an open end and a closed end with nipples for connecting respectively to a source supply suction vacuum and a collection needle.

U.S. Pat. No. 5,205,816; LAPAROSCOPIC IRRIGATOR-ASPIRATOR BLUNT DISECTOR; D. Dodson et al. This patent is directed to a laparoscopic instrument for performing blunt disection as well as irrigation and aspiration of the operative field.

U.S. Pat. No. 5,195,952; NOISE REDUCING ASPIRATOR; A. Solnit et al. This patent is directed to a noise reducing aspirator which is used to carry away air, water, saliva and includes and open-ended large tubular housing having one end adapted to be connected to a suction the other adaptively connected to an aspirator tip.

U.S. Pat. No. 5,360,414; TUBE FOR DRAINING BODY CAVITIES, VISCERA AND WOUNDS; R. J. Yarger. This patent is directed to a suction tube for removing fluid and includes an elongated tubular section with exterior and interior surfaces defining an internal tubular passageway and a plurality of radially extending, circumferentially spaced elongateds.

SUMMARY OF THE INSTANT INVENTION

There is provided a surgical suction wand comprising a tubular body having a hollow, reduced-diameter tip at one end thereof. The bore of the tip communicates into the interior of the body. A releasable cap is adapted to be attached to the other end of the body, for example by a latching, snap fit and includes a tubular connector externally thereof. A bayonet lock or other suitable connection is contemplated. The bore of the connector communicates through the cap into the interior of the body. In a preferred embodiment, the housing, i.e. the body and the cap, is fabricated of low density polyethylene, although other materials are contemplated.

A tapered filter member is located within the body. The filter member includes two planar surfaces which are joined together at one end and separated at the other end. The edges of the filter member form a snug fit with the inner surface of the body and the cap to define a first chamber between the filter member and the inner wall of the body and cap and a second chamber within the filter member. A plurality of apertures through the two planar surfaces interconnect the second chamber at the interior of the filter member with the first chamber. While not limited thereto, the filter member is, typically, fabricated of polypropylene or other suitable material.

The cap has integrally formed therein, adjacent the connector portion thereof, location means to receive and locate the other (separated) end of the filter member within the cap such that material entering the body through the tip flows into the first chamber, i.e. outside the filter member. The second chamber within the filter member is in communication with the tubular connector by way of the cap.

It will, thus, be appreciated that liquid and solid matter enter the surgical suction wand through the tip thereof and are drawn into the interior of the body. The liquid content thereof continues to flow through the apertures in the filter member into the second (or inner) chamber and, thence, through the tubular connector for collection. Conversely, the solid matter does not pass through the apertures in the filter member and is retained within the hollow interior of the body or on the outer surface of the filter member.

When the filter member becomes blocked by the accumulation of solid matter on the surface thereof, the filter member can readily be removed from the body by removing the cap, cleaned off and replaced for further use of the suction wand.

Thus, the surgical suction wand of the invention provides a controlled build-up of solid matter in a predetermined location combined with ready disposal of the solid matter quickly and with little mess.

The tubular connector may be provided with a plurality of circumferentially spaced, radially extending ribs on the outer wall thereof for purposes of strength and flexibility.

The surgical suction wand may be fabricated of a rigid or semi-rigid transparent plastic material such as polyvinyl chloride (PVC), high density polyethylene or any other suitable material. Tubular extension pieces of different shapes and lengths may be attached by a friction push-fit into the free end of the tip of the body and/or the connector.

BRIEF DESCRIPTION OF THE DRAWINGS

FIG. 1 is a partial, cross-sectional side view of a preferred embodiment of the suction wand of the instant invention.

FIG. 2 is a partial cross-sectional plan view of the suction wand of the instant invention as shown in FIG. 1.

FIG. 3 is a cross-sectional view of the filter member latch in this invention as shown in FIG. 1.

DESCRIPTION OF A PREFERRED EMBODIMENT

Referring concurrently to FIGS. 1 and 2, the surgical suction wand 10 comprises a tapering, tubular body 2 and a tip 6 at one end thereof. The tip 6 includes a central bore 8 therethrough communicating with the interior of the body 2. The body 2 tapers slightly with the internal diameter thereof increasing gradually from the tip 6.

The other end of the body 2 is connected to end cap 12 with a snap fit. For example, the end of body 2 can include a small bead 11 therearound while the cap 12 can include a channel 36 therearound which channel is adapted to receive the bead snugly. A pressure tab 7 (FIG. 1) extends radially outwardly from the end cap 12 to permit easy disengagement of the snap fit.

End cap 12 has integrally formed therewith an external, axially extending connector tube 14. The bore 16 in tube 14 communicates with the interior space of end cap 12. A plurality of circumferentially-spaced, strengthening fins 18 are provided along the connector tube 14 adjacent to the end cap 12 to provide strength and flexibility.

The suction wand 10 further includes a hollow filter element 26 which includes a pair of planar sheets 26A and 26B which, as shown in FIG. 1, are joined together at one end. (In practice, the filter element may comprise a single strip which is folded in the middle thereof to form the two sheets.)

The sheets of the filter element taper slightly from the common or closed end (which can be radiused to conform to the inner surface of the body 2) to the open end. In addition, the planar sheets 26A and 26B gradually diverge from each other. In a preferred embodiment, the wider end of filter 26, i.e. the divergent ends of the planar sheets 26A and 26B, is separated by the interlocking standoffs 59 and 60 which are mounted (or formed) on the inner surface of plates 26A and 26B, respectively. Typically, the standoffs are connected together in a push fit. The standoffs locate the planar sheets of the filter element within the body 2 and maintain chamber 31 between the sheets. Any other type of standoff can be provided to maintain the spacing between the planar sheets 26A and 26B. Of course, in the case of a rigid filter, a standoff may not be required.

The wider ends of sheets 26A and 26B are also located and secured in the latch devices 61 (see FIG. 3 for details) at the interior surface of cap 12. The free (and closed) end of the filter element 26 abuts the interior surface of body 2 and the interior end of the tip 6 to determine the axial operative position of the filter element 26 within the body 2.

As shown in FIG. 2, the edges of the planar sheets of filter element 26 snugly abut and conform to the inner surface of body 2. The common end of filter element 26 is disposed adjacent to the bore 8 in tip 6 in order to provide a diverter to cause waste matter to flow to the outer chamber 30 on either side of the filter 26.

In operative position, the filter element 26, together with the inner surface of body 2, defines chamber 30 within the body 2 (see FIG. 1). A plurality of holes 81 through the planar sheets 26A and 26B of the filter element 26 interconnect the hollow inner chamber 31 of filter element 26 with chamber 30. By altering the size, number and pattern of holes 81 in either or both of the plates 26A and 26B, the rate of flow through the suction wand can be controlled. Likewise, the efficacy and efficiency of the filter element 26 can also be controlled by adjusting the holes 81.

The bore 8 of the tip 6 communicates into outer chamber 30. The tapering shapes of body 2 and the filter element 26 are such that the transverse cross-section area of the chamber 30 decreases in size from the tip end of body 2 to the cap end thereof.

Integrally formed with the inner wall of the cap 12 are latches 61 which are provided to locate and secure the interior end of filter element 26 in the cap 12. Moreover, the latches 61 maintain the open end of the filter in place and assist (or replace) the standoffs 59 and 60 in maintaining the filter element 26 in place in the body 2.

As shown in detail in FIG. 3, each latch 61 forms a channel 161 which is fixed on the inner surface of cap 12. The channel selectively receives and secures the end of the planar sheets of filter element 26.

Conveniently, the surgical suction wand 10 is molded from a rigid, translucent plastic material such as polyethelyne. The tip 6 and the connector 16 can be relatively flexible tubular extension pieces provided in a plurality of different lengths and shapes. One end of an extension piece is adapted to engage in a close push-fit on the free end of the tip 14 of the suction wand 10. One such extension piece 44 is shown attached to tip 14. An additional extension can be found integrally or separately at tip 6.

In operation, a length of tubing (such as the extension piece 44) is attached to the connecting tube 14. The extension 14 feeds to a container (not shown) to which is also connected a suction source whereby the suction source exerts a suction effect at the tip 6 of the suction wand 10.

Thus, extraneous and/or waste material adjacent the free end of the tip 6 is drawn into the suction wand 10 along paths defined by the arrows in FIG. 1. Clearly, the liquid content of the waste matter can pass through the holes 81 in the planar plates 26A and 26B of filter element 26 and can be drawn into the container. However, gelatinous or solid matter, such as bone splinters, tissue and the like, cannot pass through the holes 81 and is, therefore, collected within the hollow chamber 30 of the suction wand 10. The build-up of such solid matter generally begins at the end of the filter element 26 adjacent the cap 12 and continues along the filter element 26 towards the end thereof adjacent the tip 6.

Ultimately, the outer chamber 30 and/or the surface (or surfaces) of the filter element 26 is substantially full of (or clogged by) waste matter and liquid flow therethrough is substantially prevented. At this time, the end cap 12 is removed from the body 2 (after the suction has been removed) and the filter element 26 (still attached to cap 2 by latches 61) is withdrawn from body 2. The body 2 is emptied and the filter element 26 is cleaned off, for example, by wiping the surfaces of plates 26A and 26B and returned into the body 2 for further utilization.

Thus, it will be appreciated that a surgical suction tip according to the invention blocks of waste matter in a controlled manner and in a predetermined location whereby unblocking of the system can be effected quickly and with little mess. In essence, removal, cleaning and replacement of the filter element 26 into body 2 is actually all that is required. This function can be quickly and easily accomplished in the environment in use.

Thus, there is shown and described a unique design and concept of surgical suction wand with a cleanable, re-usable (or disposable) filter element. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A surgical suction apparatus comprising a tubular body having an inner wall surface, a hollow tip at one end of said body which communicates into the interior of said body, a releasable cap closing the other end of said body, a tubular connector which communicates through said cap into the interior of said body, a filter member located within said body to define a chamber between said filter member and said inner wall surface of said body, said filter member includes a plurality of plate members, said filter member including a plurality of apertures therein interconnecting the interior of said filter member with said chamber, and location means integrally formed on said cap to receive and locate one end of said filter member adjacent said cap.

2. The apparatus recited in claim 1 wherein, said plate members are joined together at one end thereof.

3. The apparatus recited in claim 1 wherein, said filter member is configured to snugly abut against said inner wall surface.

4. The apparatus recited in claim 3 wherein, said body and said filter element have a tapered configuration.

5. The apparatus recited in claim 1 including, tab means on said cap to assist in releasing said cap from said body.

6. The apparatus recited in claim 2 wherein the other end of said plate members are separated to thereby define a second chamber within said filter member.

7. The apparatus recited in claim 2 wherein, said one end of said plate members is disposed adjacent to said hollow tip.

8. The apparatus recited in claim 1 wherein, said hollow tip has a smaller diameter than said tubular body.

9. The apparatus recited in claim 1 wherein, said releasable cap is selectively attached to said tubular body by a snap fit.

10. The apparatus recited in claim 1 wherein, said tubular body and said releasable cap are fabricated of polyethylene, and said filter member is fabricated of polypropylene.

11. The apparatus recited in claim 1 wherein, said tubular connector includes at least one radially extending rib to provide strength and flexibility to said tubular connector.

12. The apparatus recited in claim 6 including, spacer means interposed between said plate members at said other end in order to maintain said second chamber between said plate members.

13. A surgical suction device comprising a tubular body having an inner wall surface, a releasable cap selectively closing one end of said body, a filter member disposed within said body to define a first chamber between said filter member and said inner wall surface of said body, said filter member comprising a plurality of planar members and including a second chamber therein intermediate said planar members, said filter member including a plurality of apertures therein for interconnecting said second chamber at the interior of said filter member with said first chamber, and positioning means integrally formed on said cap to position said filter member adjacent to said cap and said body to filter material passing through said body and said cap.

14. The device recited in claim 13 wherein, one end of said filter member is closed and the other end thereof is open.

15. The device recited in claim 13 including, a hollow tip at one end of said body which communicates with the interior of said body, and a tubular connector which communicates through said cap into the interior of said body.

16. The device recited in claim 13 wherein, said cap has an arcuate configuration.

17. The device recited in claim 16 wherein, said positioning means is formed within the arcuate configuration of said cap.

18. The device recited in claim 13 wherein, said first chamber is a substantially closed space between said filter member and said inner wall of said tubular body.

19. The device recited in claim 13 wherein, said plurality of planar members comprise a unitary planar member folded over on itself.

20. A surgical suction device comprising a tubular body having an inner wall surface, a releasable cap selectively closing one end of said body, and a filter member disposed within said tubular body and configured so that the outer edges thereof snugly abut said inner wall surface of said tubular body thereby to define a first chamber betweeen said filter member and said inner wall surface of said tubular body, said filter member including a second chamber therein, said filter member including at least one aperture therein for interconecting said second chamber at the interior of said filter member with said first chamber.

\* \* \* \* \*